(12) United States Patent  
Kenk et al.

(10) Patent No.: US 9,119,688 B2  
(45) Date of Patent: Sep. 1, 2015

(54) HOLDING DEVICE FOR DENTAL IMPLANT

(75) Inventors: Frank Kenk, Basel (CH); Stéphane Courvoisier, Basel (CH); Guillaume Bugnard, Basel (CH); Miodrag Lazic, Basel (CH)

(73) Assignee: STRAUMANN HOLDING AG, Basel (CH)

( * ) Notice: Subject to any disclaimer, the term of this patent is extended or adjusted under 35 U.S.C. 154(b) by 84 days.

(21) Appl. No.: 13/409,699

(22) Filed: Mar. 1, 2012

(65) Prior Publication Data

US 2013/0230825 A1  Sep. 5, 2013

(51) Int. Cl.  
*A61C 8/00* (2006.01)

(52) U.S. Cl.  
CPC ............ *A61C 8/0087* (2013.01); *A61C 8/0089* (2013.01)

(58) Field of Classification Search  
CPC .............................. A61C 8/0089; A61C 8/0087  
USPC ............................. 433/141, 173, 174; 206/368  
See application file for complete search history.

(56) References Cited

U.S. PATENT DOCUMENTS

| | | | |
|---|---|---|---|
| 5,622,500 A * | 4/1997 | Niznick | 433/173 |
| 5,692,904 A * | 12/1997 | Beaty et al. | 433/141 |
| 6,206,696 B1 * | 3/2001 | Day | 433/141 |
| 6,217,332 B1 * | 4/2001 | Kumar | 433/173 |
| 6,247,932 B1 * | 6/2001 | Sutter | 433/173 |
| 6,261,097 B1 * | 7/2001 | Schmutz et al. | 433/173 |
| 6,315,562 B1 * | 11/2001 | Kumar | 433/173 |
| 6,332,777 B1 * | 12/2001 | Sutter | 433/173 |
| 6,416,324 B1 * | 7/2002 | Day | 433/173 |
| 7,484,959 B2 * | 2/2009 | Porter et al. | 433/173 |
| 8,070,491 B2 * | 12/2011 | Mundwiler et al. | 433/163 |

* cited by examiner

*Primary Examiner* — Ralph Lewis (74) *Attorney, Agent, or Firm* — Scully, Scott, Murphy & Presser, P.C.

(57) ABSTRACT

A holding device for retaining and transporting a dental implant, particularly a dental implant stored in an ampule having preserving fluid, is provided. The holding device has a securing section, which has a force transmission element for rotationally securing the dental implant and an attachment element having one or more resilient arms formed integrally with and distally of the force transmission element, for longitudinally retaining the dental implant. The resilient arms do not extend beyond the radial perimeter of the force transmission element. The resilient arms can be transformed between a first operative configuration and a second compressed configuration under forces during operation, to allow a radially enlarged end of the arms to releasably engage an undercut of the dental implant.

23 Claims, 11 Drawing Sheets

HOLDING DEVICE FOR DENTAL IMPLANT

FIELD

The present disclosure relates generally to an improved holding device for a dental implant, and more particularly, to an improved coupling of the holding device to the dental implant.

BACKGROUND

As known in the industry, dental implants can be stored prior to their use in a sealed container, which is preferably filled with a storage fluid, as disclosed in U.S. Pat. No. 6,261,097B1, which is commonly assigned with the assignee of the present application and the entire disclosure of which is incorporated herein for all purposes.

During storage, a dental implant is temporarily coupled to a holding device, which firmly retains the dental implant in position within an ampule within the container. When the dental implant is removed from the ampule for implantation into a jawbone, the holding device can be gripped by a user for positioning at an implant site. Furthermore, the holding device is adapted to enable a temporary yet positive engagement with a manipulating tool, which facilitates the removal of the dental implant from the ampule and the placement thereof into the bone at the implant site. Ultimately, when the dental implant is implanted at the desired site in the bone, the holding device can be removed from the dental implant. Nevertheless, as the holding device is screwed to the dental implant, the overall handling is tedious.

International Publication No. WO-A1-2005/037126, which is also commonly assigned and the entire disclosure of which is incorporated herein for all purposes, discloses a holding device wherein the use of a screw for coupling the holding device to the dental implant is avoided.

Figure 1:
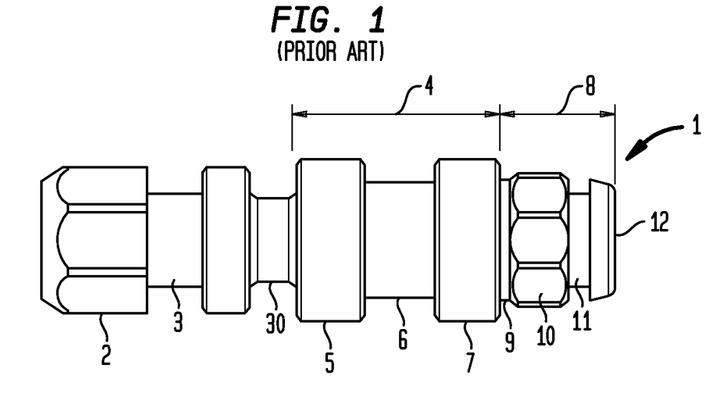
FIG. 1 is a front elevation view of a prior art holding device for a dental implant.
Figure 2:
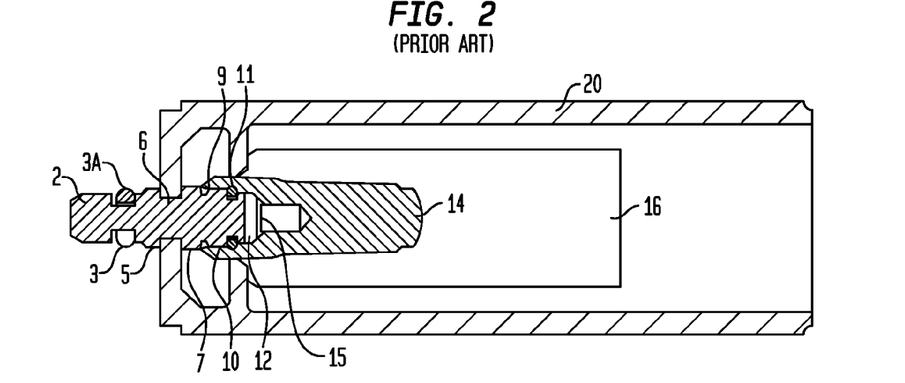
FIG. 2 is a longitudinal sectional view of the holding device coupled with a dental implant and placed in an inner ampule for storage and transportation of the dental implant.
Figure 3:
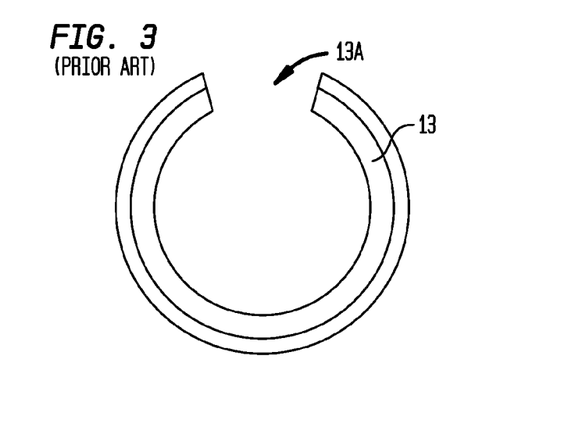
FIG. 3 is a top view of a PEEK clamping or locking ring of the prior art holding device.

As shown in FIGS. 1-3, the holding device, which is generally designated by reference numeral 1, includes an engagement section 2 adapted for positive engagement with a manipulating tool (not shown). The engagement section 2 is embodied as a polygonally shaped end, for instance, an octagonally shaped end. As shown in FIG. 2, a circumferential groove 3 is provided adjacent the engagement section 2 for accommodating an O-ring 3A, which has a securing function to the manipulating tool.

Figure 1A:
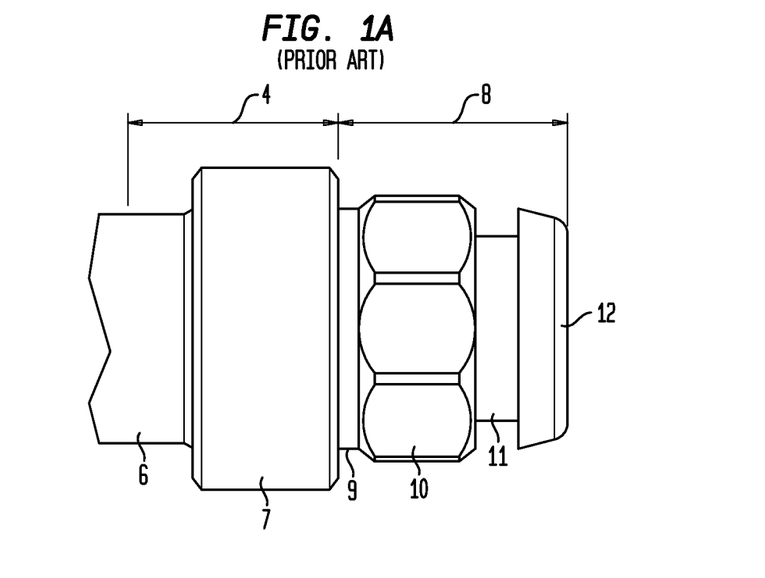
FIG. 1A is a partial enlarged view of a clamping section and a retention section of the holding device shown in FIG. 1.

Furthermore, as shown in FIGS. 1 and 1A, the holding device 1 includes a retention section 4 having two annular shoulders 5 and 7 adjoined by an intermediate cylindrical section 6 having a reduced diameter. The retention section 4 is adapted to engage an inner ampule 20. The retention section 4 is joined to the engagement section 2 by a breaking point 30.

The holding device 1 further includes a clamping section 8 adjacent to the retention section 4. The clamping section 8 includes a first circumferential groove 9, a force transmission element 10 having an octagonal shape for positive engagement with a dental implant 14, a second circumferential groove 11 and a tapered member 12. As shown in FIG. 3, the second circumferential groove 11 is provided with a clamping or locking ring 13 made of PEEK (poly ether ether ketone), which includes a peripheral clearance 13A for facilitating the mounting thereof.

Figure 2A:
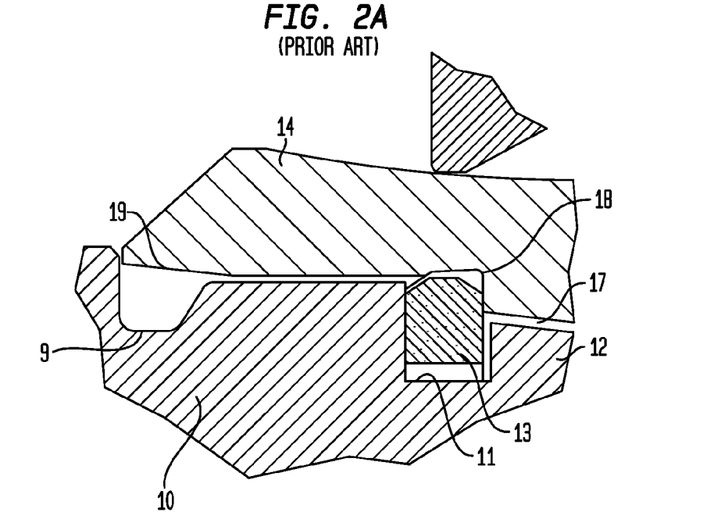
FIG. 2A is a partial enlarged longitudinal sectional view illustrating the coupling of the holding device to the dental implant.

As shown in FIG. 2, the dental implant 14 includes a cavity 15 having an inner surface 17 that matches the outer surface of the force transmission element 10, such that a positive engagement between the dental implant 14 and the holding device 1 can be provided to allow the dental implant 14 to be rotationally secured to the holding device 1. As shown in FIG. 2A, the cavity 15 of the dental implant 14 further includes an undercut 18 dimensioned to clampingly receive the lock ring 13, and a conical terminal section 19 enclosing the first circumferential groove 9 of the clamping section 8 of the holding device 1.

Certain disadvantages have been identified from the known holding devices. For example, the clamping force of the PEEK locking ring 13 changes with time or is variable ab initio. Thus, it is difficult to precisely adjust the clamping force when the implantation is carried out. This problem is pronounced, if the dental implant is stored over a long time span, and is even further aggravated if the storage medium is a fluid. Furthermore, the prior art locking ring tends to release carbon, which may damage the surface of the dental implant, particularly dental implant surfaces treated in order to improve bone cell attachment, for example sandblasted and/or acid etched and/or coated surfaces. In addition, the manufacturing tolerances of the PEEK locking ring are very strict, and therefore the production thereof may become difficult.

U.S. Pat. No. 8,070,491, which is also commonly assigned and the entire disclosure of which is incorporated herein for all purposes, discloses a holding device which includes a separately formed clamping member 113 made of a plastic material or a clamping member 223 in the shape of an arm milled from a lateral wall of a force transmission element 210. Both clamping members 113 and 223 extend in their non-compressed state beyond the perimeter of the force transmission element. This enables the members to snap into an implant undercut 18 directly distally adjacent to the area of the inner implant surface 17 that matches the force transmission element 110, 210 of the holding device. For the holding device having a separately formed clamping member, additional steps of manufacturing and attaching the clamping member are required, which compromises the integrity and operability of the holding device and also increases the cost of manufacture. Furthermore, it has been found that the separate plastic component shrinks over time and thus, loses its ability to securely grip the dental implant. In addition, in order to connect the separately formed clamping member to the holding member, the force transmission element must be at least partially hollow, thus reducing the strength of this element. This same problem occurs when the clamping member is milled from the lateral wall of the force transmission element, namely the strength of the force transmission element is reduced due to the milled lateral wall thereof. Furthermore, the arm-shaped clamping member, milled from the lateral wall of the force transmission element, may suffer from distortion during the rotation of the force transmission element, which can lead to disconnection of the milled arm(s) from the dental implant. In addition, the process of milling an arm from the lateral wall of the force transmission element requires additional steps.

Therefore, it is desirable to provide an improved holding device, which overcomes one or more of the disadvantages of the known holding devices.

BRIEF DESCRIPTION OF THE DISCLOSURE

As described herein, the exemplary embodiments of the current disclosure overcome one or more of the above or other disadvantages known in the art.

One exemplary aspect of the present disclosure relates to a holding device for a dental implant, the holding device extending along a longitudinal axis and having a proximal end and a distal end. The holding device includes an engagement section provided at the proximal end, adapted to engage a manipulating tool; a retention section distally connected to the engagement section and adapted to engage a package; and a securing section distally connected to the retention section and adapted to couple the holding device to the dental implant. The securing section includes a force transmission element adapted to rotationally secure the dental implant and an attachment element provided distally of the force transmission element adapted to longitudinally secure the dental implant. The force transmission element has a first projected area in a plane substantially perpendicular to the longitudinal axis and the attachment element has a second projected area in the plane. The second projected area is defined within the first projected area. The attachment element includes at least one resilient arm adapted to longitudinally retain the dental implant, the at least one resilient arm comprising a first operative configuration and a second compressed operative configuration.

Another exemplary aspect of the present disclosure relates to a combination of a holding device and a dental implant, the combination extending along a longitudinal axis and having a proximal end and a distal end. The holding device includes an engagement section provided at its proximal end and adapted to engage a manipulating tool; a retention section distally connected to the engagement section and adapted to engage a package; and a securing section distally connected to the retention section and adapted to couple the holding device to the dental implant. The dental implant includes a cavity for at least partially receiving the securing section of the holding device. The securing section includes a force transmission element adapted to rotationally secure the dental implant and an attachment element provided distally of the force transmission element adapted to longitudinally secure the dental implant. The force transmission element has a first projected area in a plane substantially perpendicular to the longitudinal axis and the attachment element has a second projected area in the plane. The second projected area is defined within the first projected area. The attachment element includes at least one resilient arm adapted to longitudinally retain the dental implant. The resilient arm includes a first operative configuration and a second compressed operative configuration. The cavity of the dental implant comprises an anti-rotation section, which is shaped to non-rotationally engage with the force transmission element and, distal of and non-adjacent to the anti-rotation section, an undercut, said undercut having a diameter less than that of the anti-rotation section.

Thus, in accordance with the present disclosure the attachment element is located distal of and does not extend beyond the perimeter of the force transmission element.

In an exemplar embodiment, the at least one resilient arm of the attachment element is integrally formed with the force transmission element.

Throughout this specification, references to "provided/connected distal of/to" or "provided/connected proximal of/to" describe the relative placements of various features of the holding device and implant. However, it is not necessary for the such-described features to be in direct sequence with one another, and intervening or intermediate features may exist unless the features are described as being "directly" distally/proximally provided/connected or "directly adjacent" to one another.

BRIEF DESCRIPTION OF THE DRAWINGS

Further characteristics and advantages of the present disclosure will become apparent from the following description of some exemplary but not exclusive embodiments of a holding device for a dental implant, illustrated by way of non-limitative examples in the accompanying drawings, wherein.

DETAILED DESCRIPTION

Figure 4:
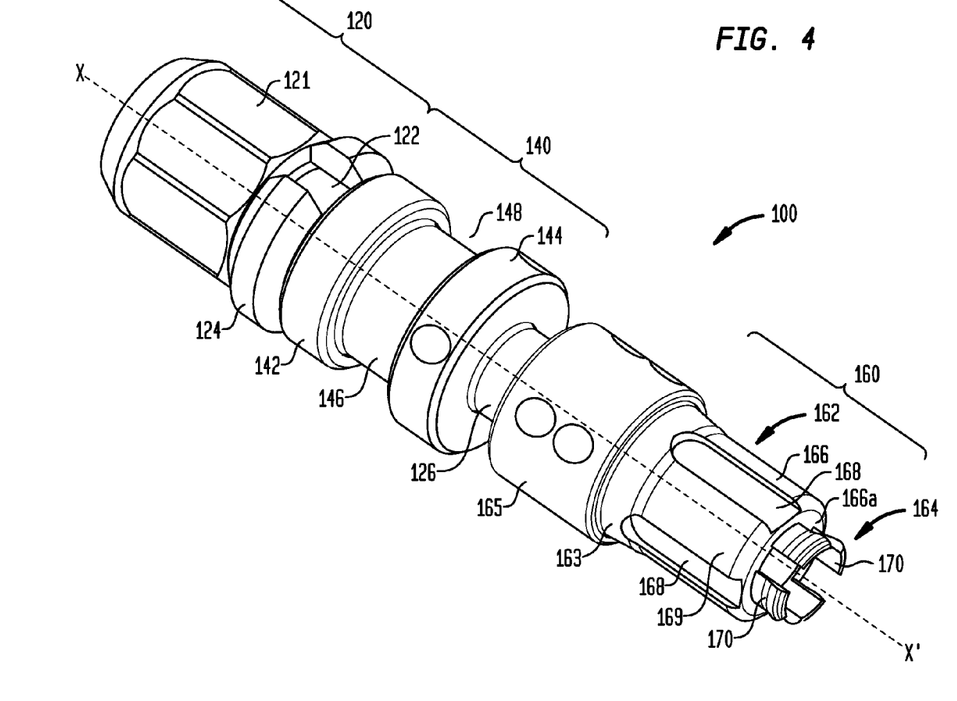
FIG. 4 is a perspective view of a holding device according to an exemplary embodiment of the present disclosure.
Figure 5:
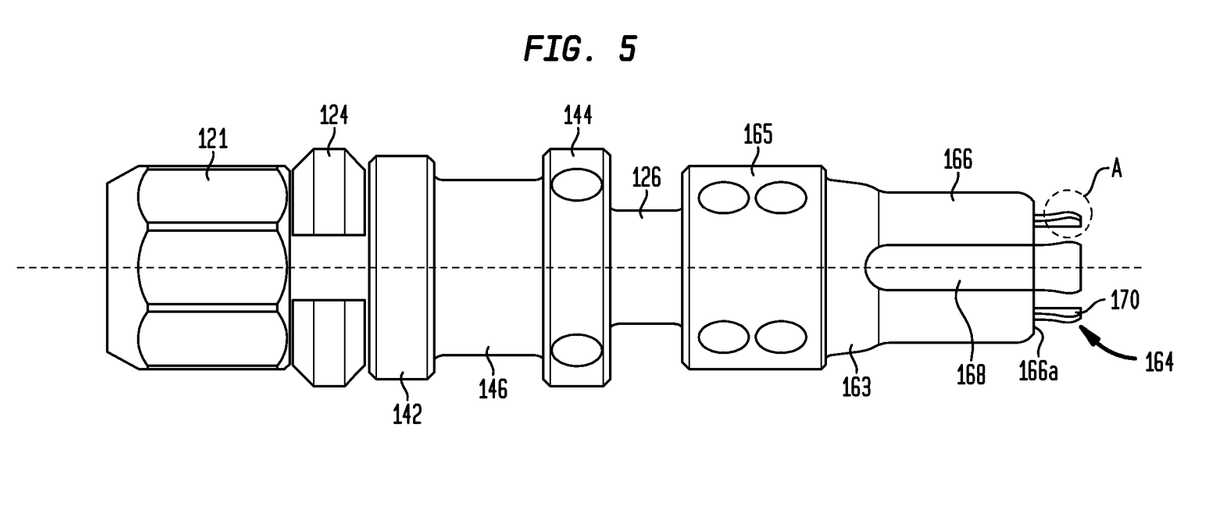
FIG. 5 is a front elevation view of the holding device shown in FIG. 4.

FIG. 4 is a perspective view illustrating a holding device 100 according to an exemplary embodiment of the disclosure. FIG. 5 is a front elevation view of the holding device 100. The holding device 100 is elongated along a longitudinal axis X-X'. The holding device 100 is substantially radially symmetrical about the axis X-X'. The holding device 100 includes, from the proximal end thereof (close to a hand of a user) to the distal end thereof (away from the hand of the user), an engagement section 120 adapted to engage either directly or indirectly a manipulating tool (such as, a screw driver), a retention section 140 adapted to engage a package (such as, an ampule), and a securing section 160 adapted to engage a dental implant.

The engagement section 120 enables the holding device 100 to be longitudinally secured to a manipulating tool and for torque to be transmitted from the tool to the device. The engagement section 120 has an external profile 121 suitable for transferring torque from a manipulating tool, e.g. a dental hand piece, ratchet, or manual handle to the holding device. The external profile 121 can be a polygonal (such as, octagonal) external profile or comprise alternating grooves and protrusions for engaging directly or indirectly the manipulating tool. A circumferential groove 122 can be provided distally adjacent to the external profile 121, into which a securing element (such as, an O-ring 124 made of PEEK) can be placed. Alternatively the engagement section 120 may comprise a standard ISO latch configuration.

The retention section 140 includes a first annular shoulder 142 and a second annular shoulder 144, longitudinally connected to each other through an intermediate cylindrical element 146 having a reduced diameter with respect to the shoulders. A circumferential groove 148 is defined by the first annular shoulder 142, the intermediate cylindrical element 146 and the second annular shoulder 144. The groove 148 functions to receive a mating structure, such as a flange, of an external package to allow the dental implant to be positioned within the package. The retention section 140 is connected to the securing section 160 through a section of narrowed diameter which forms a break point 126 in the holding device 100. This break point 126 is designed to shear or distort upon application of a pre-determined excessive torque. The pre-determined torque is selected such that the break point 126 will break before the excessive torque damages the implant.

Figure 8:
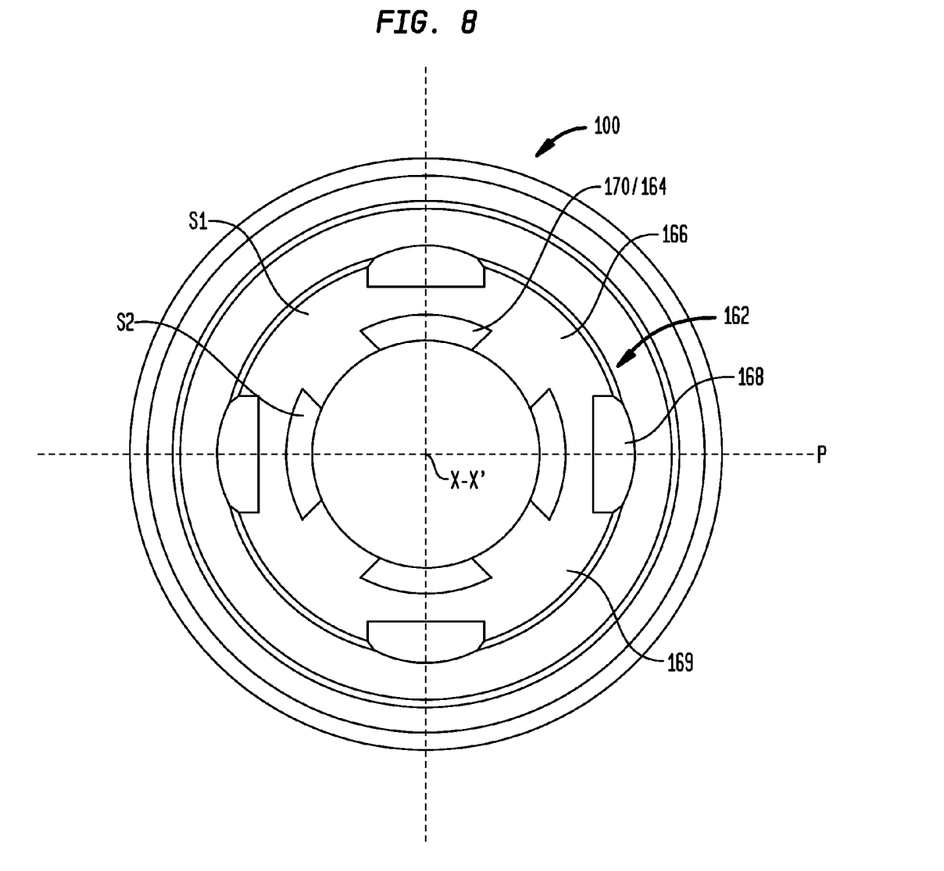
FIG. 8 is a side elevation view of the distal end of the holding device shown in FIG. 1.

The securing section 160 includes, but is not limited to, a section providing clamping, gripping, fastening and/or locking functionalities. The securing section 160 includes a force transmission element 162 for rotationally securing a dental implant, a transitioning element 163 connecting the force transmission element 162 to the distal end of a third annular shoulder 165, and an attachment element 164 integrally formed with the distal end of the force transmission element 162 for longitudinally retaining the dental implant. The transitioning element 163 can have a substantially conical profile. The force transmission element 162 includes a substantially cylindrical body 166 and one or more grooves 168 formed into the cylindrical body 166, which grooves extend longitudinally from the distal end surface 166a of the cylindrical body 166 toward the retention section 140. As best shown in FIG. 8, the grooves 168 can be provided circumferentially about the cylindrical body 166 and evenly spaced about the longitudinal axis X-X'. Each two adjacent grooves 168 define a projection 169. Thus, the grooves 168 and the projections 169 are alternately disposed along the perimeter of the cylindrical body 166.

Referring to FIGS. 6, 6A, 7, 7A and 9, a dental implant 200 according to another aspect of the disclosure is illustrated. The dental implant 200 has a longitudinally extending cavity 210, into which the securing section 160 of the holding device 100 is inserted to operatively couple the holding device 100 to the dental implant 200. At the proximal end of the dental implant 200, the cavity 210 has a substantially conical section 220, which aligns with and may co-operate with the outer profile of the transitioning element 163 when the securing section 160 has been fully inserted into the cavity 210.

Figure 6:
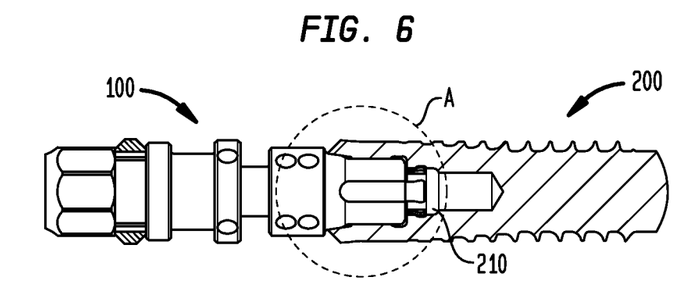
FIG. 6 is a front view of a combination of the dental implant shown in FIG. 5 and a dental implant shown in a longitudinal cross section according to another aspect of the present disclosure.
Figure 6A:
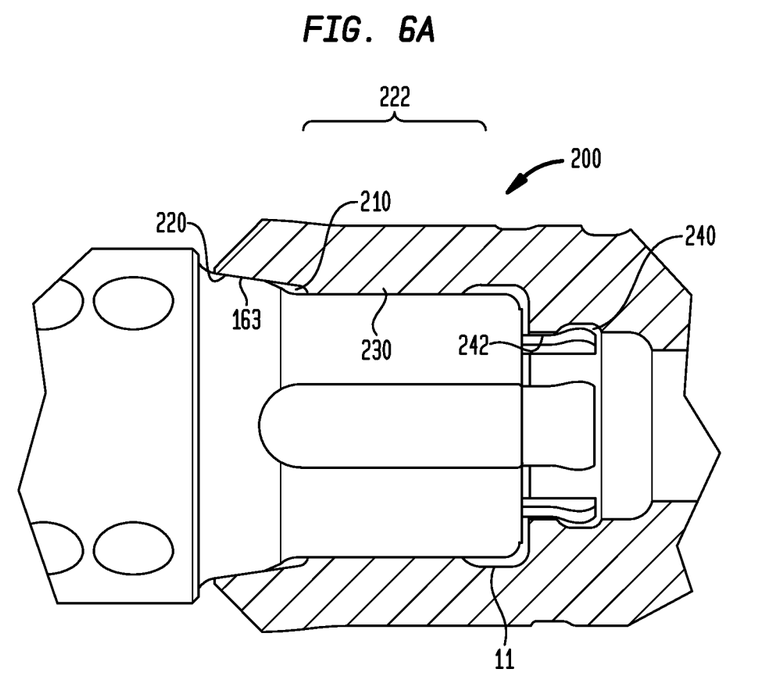
FIG. 6A is a partial enlarged view of the coupled holding device and dental implant shown in FIG. 6.
Figure 7:
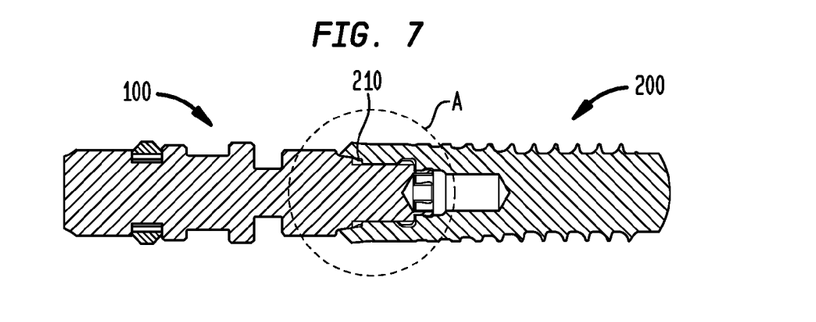
FIG. 7 is a longitudinal sectional view of the coupled holding device and dental implant shown in FIG. 6.
Figure 7A:
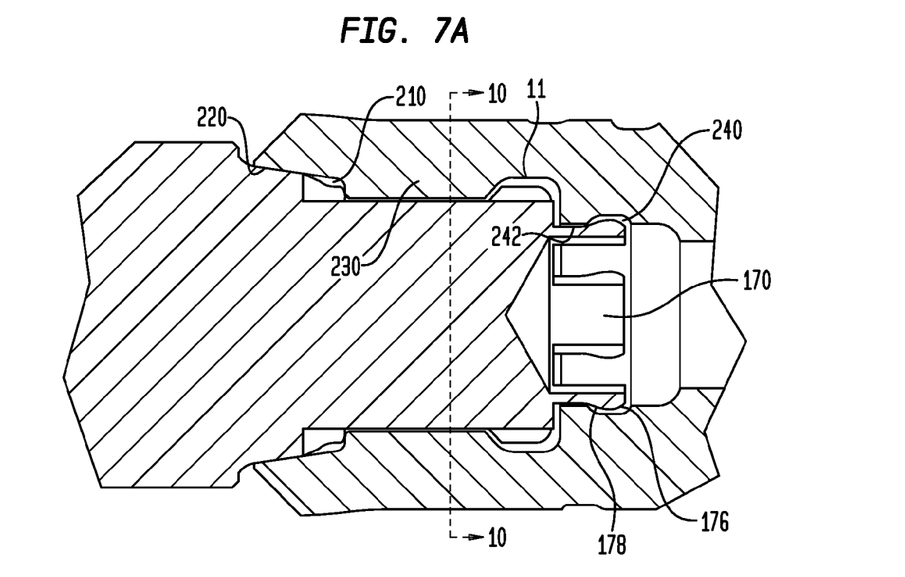
FIG. 7A is a partial enlarged view of the coupled holding device and dental implant shown in FIG. 7.
Figure 9:
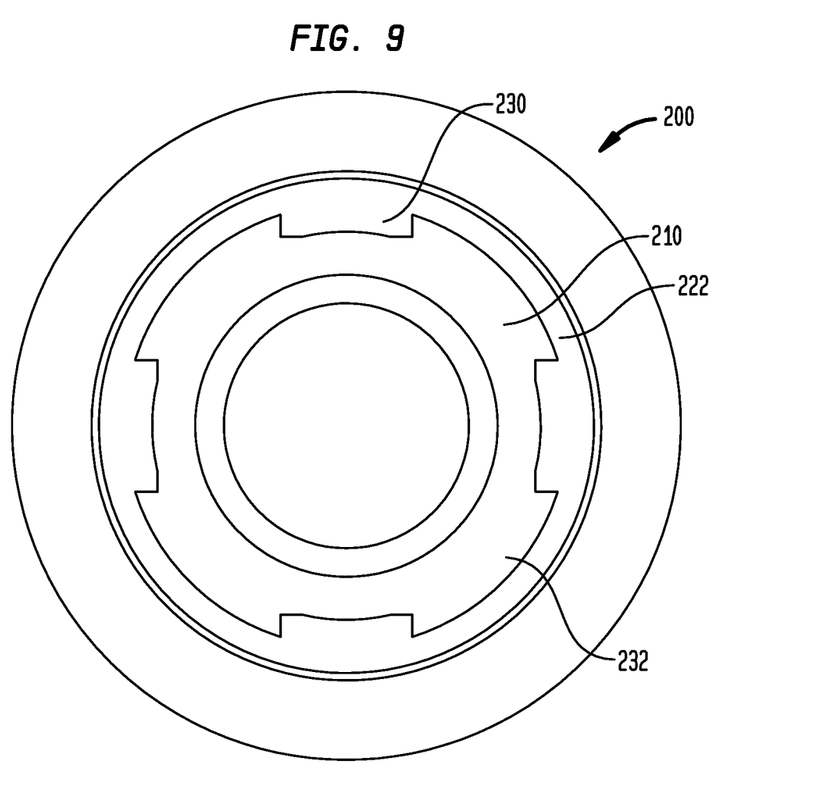
FIG. 9 is a side elevation view of the proximal end of the dental implant shown in FIG. 6.

As best shown in FIGS. 6A and 9, the dental implant 200 includes an anti-rotation section 222, which during operation mates with the force transmission element 162 to implement a rotationally secure engagement between the dental implant 200 and the holding device 100 such that relative rotation between the implant and holding device is limited or prevented. In the shown embodiment, the anti-rotation section 222 includes one or more elongated projections 230, which extend longitudinally within the cavity 210. The projections 230 can be provided along the inner circumference of the dental implant 200 and equally spaced about the longitudinal axis X-X'. The anti-rotation section 222 further includes one or more longitudinal grooves 232 defined by two adjacent projections 230.

Figure 10:
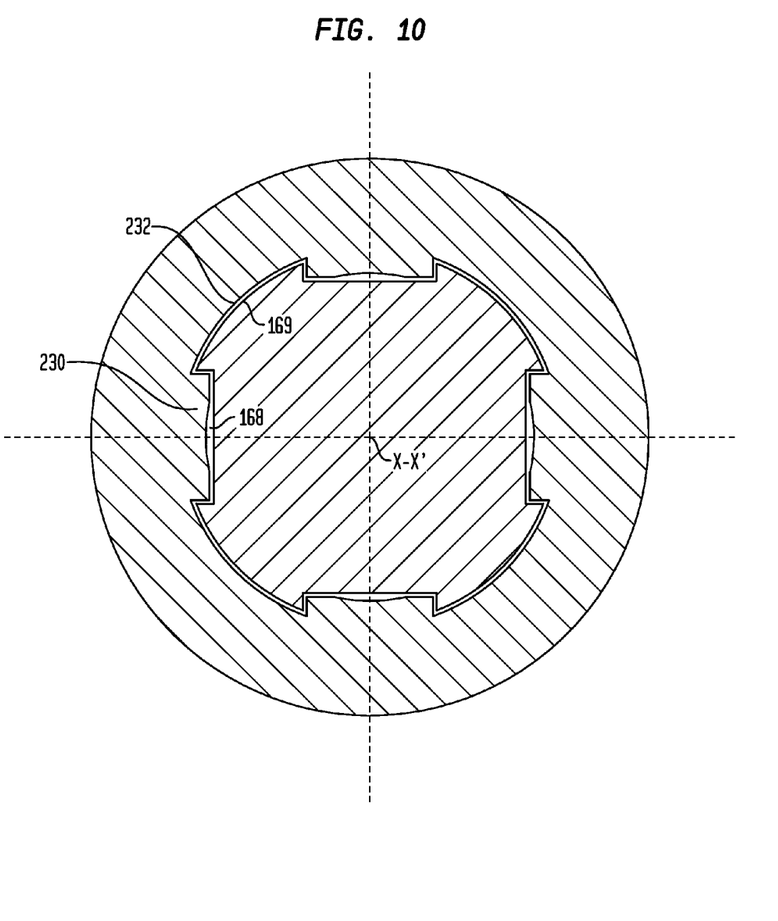
FIG. 10 is a radial sectional view of the coupled holding device and dental implant along Lines 10-10 shown in FIG. 7A.

As shown in FIG. 10, the position and dimension of the projections 230 of the implant 200 and the grooves 168 of the holding device 100 are selected, such that, when the force transmission element 162 is inserted into the cavity 210, each projection 230 is placed within a corresponding groove 168 to implement a positive rotational engagement therebetween. Similarly, the position and dimension of the projections 169 and the grooves 232 are selected, such that, when the force transmission element 162 is inserted into the cavity 210, each projection 169 is placed within a corresponding groove 232 to implement a positive rotational engagement therebetween. Accordingly, the implant can be held in a rotationally fixed position within the packaging and a rotational force can be transmitted from the holding device 100 to the dental implant 200 for the purpose of inserting the dental implant into the bone.

Figure 11:
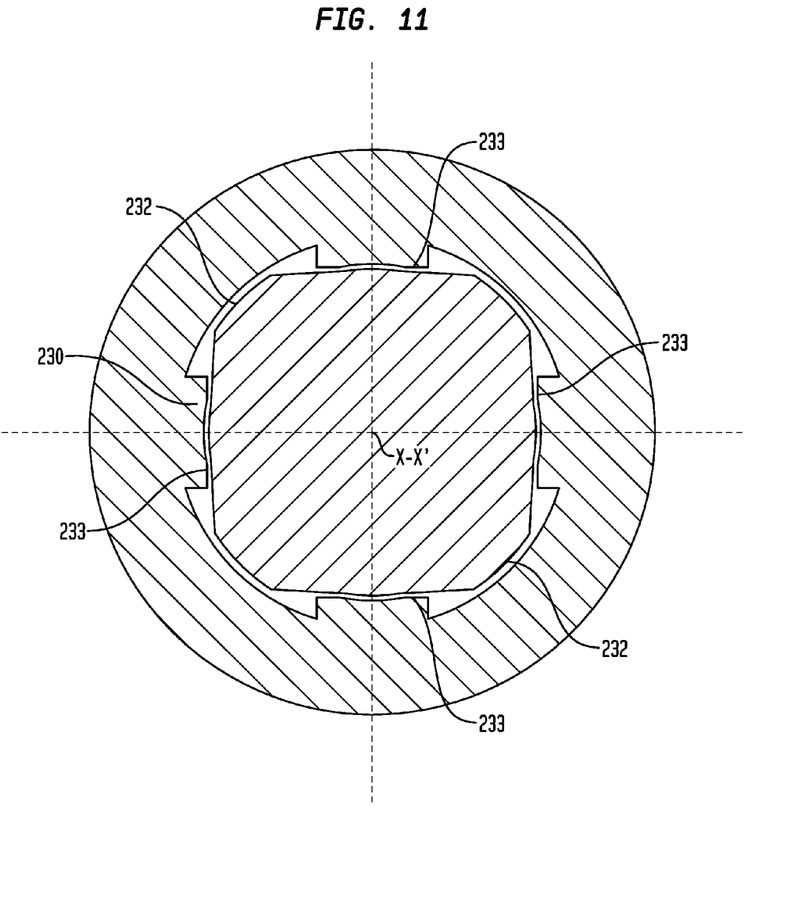
FIG. 11 is a radial sectional view of a coupled holding device and dental implant according to another exemplary embodiment.
Figure 12:
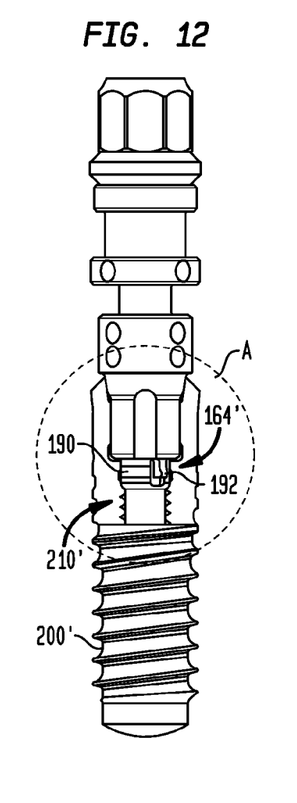
FIG. 12 is front elevation view illustrating a coupled holding device and dental implant according to yet another exemplary embodiment.
Figure 12A:
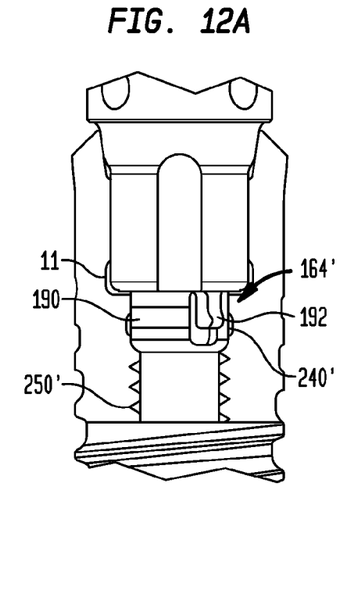
FIG. 12A is a partial enlarged view of the embodiment shown in FIG. 12.
Figure 13:
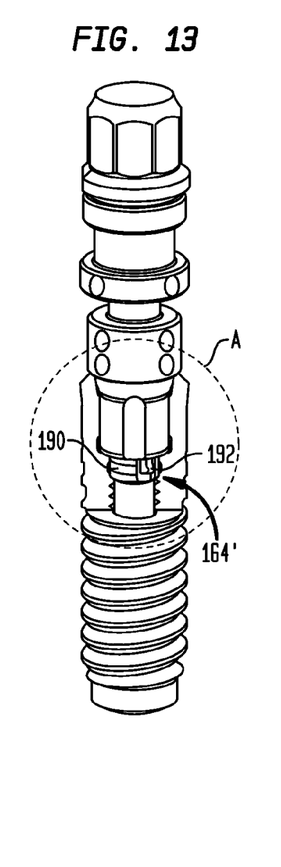
FIG. 13 is a perspective view of the embodiment shown in FIG. 12.
Figure 13A:
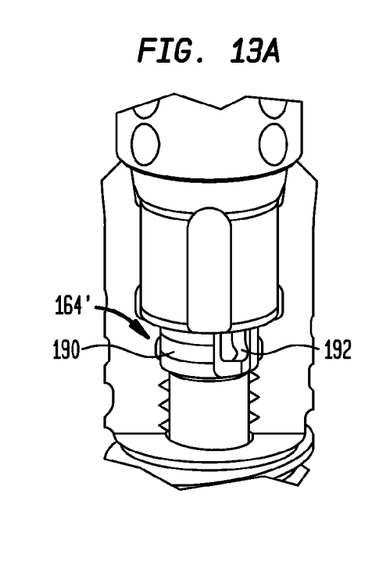
FIG. 13A is a partial enlarged view of the embodiment shown in FIG. 13.

Although a mating configuration of projections and grooves has been shown in the exemplary embodiment, a person of ordinary skill in the art understands that the mating configuration between the force transmission element 162 and the anti-rotation section 222 is not limited to the shown embodiment. In addition, the number and the profile of the projections and the grooves can be varied without departing from the spirit of the disclosure. For example, the force transmission element 162 can be designed to engage only the radially innermost sides 233 of the protrusions 230, such that the force transmission element 162 of the holding device 100 has a cross-section which is substantially square with rounded corners, as shown in FIG. 11; alternatively, the force transmission element 162 of the holding device 100 and the anti-rotation section 222 of the implant 200 can be polygonal, such as the octagonal force transmission element 10 shown in FIG. 1. Numerous co-operating force transmission elements and anti-rotation sections are known from the prior art.

Referring back to FIGS. 4, 5 and 5A, the attachment element 164 includes one or more resilient arms 170, which extend longitudinally from the distal end surface 166a of the cylindrical body 166 of the force transmission element 162. The resilient arms 170 function to longitudinally couple the holding device 100 to the dental implant 200.

The one or more resilient arms 170 are located distally of the force transmission element 162 and can be formed integrally with the force transmission element 162. Compared to the known holding devices having separately formed clamping arms made of a plastic material, the holding device according to this exemplary embodiment offers at least the following advantages. For example, there is no need for additional steps to separately manufacture the clamping arms and to attach the clamping arms to the holding device. Additionally, integrally formed resilient arms are structurally more secure. When the holding device is formed from metal, e.g. Ti or Ti alloy, since the resilient arms are integrally formed from the same metal material, certain disadvantages inherent with plastic resilient arms can be overcome, such as shrinkage over time to lose the ability to securely grip the dental implant and carbon release from PEEK components.

Compared to the known holding devices having clamping arms milled from the lateral wall of the force transmission element, or which otherwise protrude radially from the force transmission element, the holding device according to this embodiment offers at least the following advantages. For example, the integrity and strength of the force transmission element can be maintained satisfactorily, because the resilient arms are located distal of the force transmission element and hence, the force transmission element can have a solid or substantially solid structure without hollow bores or carving-outs, as can be seen from FIG. 7A. In particular, the force transmission element can be solid over at least three quarters of its length. In particular, when the holding device 100 is fully inserted into the implant 200, the section of the force transmission element which aligned with the anti-rotation section of the implant, i.e. protrusions 230, is solid. Furthermore, the resilient arms and the force transmission element are structurally separated, which allows each component to be designed based on the intended functionality thereof. According to this embodiment, the force transmission element is designed to designatedly implement a rotationally secure connection and the resilient arms are designed to designatedly implement an axial (longitudinally secure) connection, without interfering with each other. Thus, a satisfactory fit between the force transmission element and the anti-rotation section of the dental implant can be realized, and a consistent pull-off force (such as, for example, a pull-off force of 3-8N) to disengage the holding device from the dental implant can also be realized. In addition, certain disadvantages inherent with the milled resilient arms can be overcome, such as distortion of the resilient arms during the rotation of the force transmission element and undesirable dislocation of the holding device with respect to the dental implant.

Referring to FIG. 8, the location and the dimension of the one or more resilient arms 170 (or the single resilient arm 192, as shown in a later embodiment) are configured, such that the resilient arms 170 do not extend radially beyond the perimeter of the force transmission element 162. With this configuration, the arms 170 are prevented from contacting the anti-rotation section 222 of the dental implant 200, when the holding device 100 is inserted into the dental implant 200. Accordingly, there are no potential opportunities to damage either the anti-rotation section 222 or the arms 170. As shown in FIG. 8, the force transmission element 162 has a first projected area S1, which is formed in a plane P substantially perpendicular to the longitudinal axis X-X'. The first projected area S1 is defined by the perimeter of the force transmission element 162 projected on the plane P. The attachment element 164 (i.e., the plurality of resilient arms 170) has a second projected area S2 on the plane P, which is defined by the perimeter of the attachment element 164 projected on the plane P (i.e., the collective projected areas of each resilient arm). The second projected area S2 is confined within the first projected area S1, such that no part of the attachment element 164 extends beyond the radial circumference of the force transmission element 162. This is possible as the attachment element 164 is adapted to longitudinally secure the holding device 100 to the implant 200 via an undercut 240 having a diameter less than that of the anti-rotation section 222.

Figure 5A:
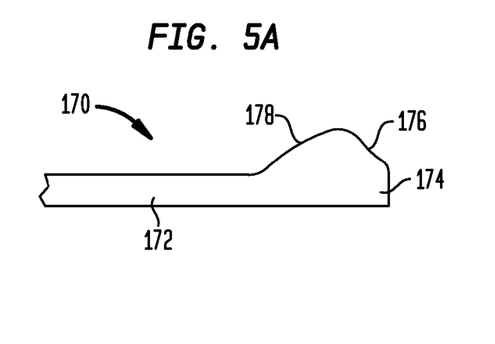
FIG. 5A is partial enlarged view of an embodiment of a resilient arm of the holding device shown in FIG. 5.

As best shown in FIG. 5A, each arm 170 includes a base 172 and a radially enlarged locking end 174 integral with the base 172. The locking end 174 has a first sloped surface 176 and a second oppositely sloped surface 178, both angled with respect to the base 172. The resilient arms 170 can be circumferentially distributed along a predetermined circle and evenly spaced about the longitudinal axis X-X'. The resilient arms 170 can be formed from a substantially cylindrical wall by removing the material between two adjacent arms.

FIGS. 12, 12A, 13 and 13A illustrate another embodiment of the holding device, in which the attachment element 164' includes a cylindrical wall 190 and a single arm 192 formed from or within the cylindrical wall 190. The single arm 192 can have same or similar structure of the resilient arms 170. Implant 200' is, for all practical purposes, identical to implant 200, with the exception that cavity 210' has an internally threaded section 250' located distally of undercut 240'.

Referring to FIGS. 6, 6A, 7 and 7A, the dental implant 200 further includes an undercut 240 distal of and remote from the anti-rotation section 222, which is adapted to operatively receive the radially enlarged locking ends 174 of the resilient arms 170. Undercut 240 is formed within a circular cylindrical section 242 of the cavity 210 having smooth walls and a smaller diameter than anti-rotation section 222. Undercut 240 is also dimensioned such that it has a smaller diameter than the anti-rotation section 222. During operation, as the securing section 160 is advanced into the cavity 210, the first slope surface 176 comes into engagement with circular cylindrical section 242 of the dental implant 200, which is directly adjacent to the undercut 240. The engagement between the first sloped surface 176 and the circular cylindrical section 242 resiliently deflects the resilient arms 170 radially inwardly. Accordingly, the resilient arms 170 are transformed from a normal configuration to a compressed configuration, such that the locking ends 174 of the resilient arms 170 can pass clear of cylindrical section 242 and be subsequently snapped into the undercut 240 to provide a positive longitudinal coupling of the holding device 100 to the dental implant 200. Once the locking ends 174 have been fully placed into and longitudinally aligned with the undercut 240, the resilient arms 170 return to either their original configuration or an intermediate configuration which is partially compressed. In this way, the resilient arms 170 are compressed during insertion of the force transmission element 162, and upon longitudinal alignment with the undercut 240, return to or at least toward the normal non-compressed configuration. When the resilient arms 170 are in the partially compressed intermediate configuration after being longitudinally aligned with the undercut 240, the arms 170 provide a radially outward pressure to the implant and thus provide a firmer retention of the dental implant. When the resilient arms 170 are in their original configuration after being longitudinally aligned with the undercut 240, a longitudinal coupling is achieved which does not place radial forces on the implant 200. Either alternative can be used depending on the design considerations and desires of the skilled person.

When detaching the holding device 100 from the dental implant 200, the holding device 100 is pulled proximally to render the second sloped surface 178 to come into engagement with the circular cylindrical section 242. Similarly, the engagement between the second sloped surface 178 and the circular cylindrical section 242 resiliently deflects the resilient arms 170 radially inwardly, to transform the resilient arms 170 from the normal or intermediate configuration to the compressed configuration. Accordingly, the locking ends 174 can pass clear the cylindrical section 242, and be subsequently withdrawn from the cavity 210 to release the attachment between the holding device 100 and the dental implant 200 and to return the resilient arms 170 to their original configuration. For example, the pull-off force to detach the holding device 100 from the dental implant 200 can be within the range of 3-8 N.

The material and the dimension of the resilient arms 170 are selected to permit predetermined radial deflection of the arms under predetermined forces, while still maintaining a satisfactory engagement between the holding device and the dental implant to avoid unintentional or accidental detachment of the holding device from the dental implant.

The combination of the resilient arms 170 and the undercut 240 offers further advantages not available to the known devices. As shown in FIG. 6A, the undercut 240 is disposed distally to the anti-rotation section 222 of the dental implant 200. Thus, the axial retention of the dental implant 200 occurs deeper within the cavity 210 of the dental implant, as compared to the known holding devices discussed previously, which results in a more secure connection less liable to disconnection due to longitudinal displacement between the implant and the holding device.

In addition, for the known assembly as shown in FIG. 2A, the undercut 11 of the dental implant 14 is formed directly distal of the anti-rotation section of the dental implant. Thus the undercut 11 has a larger diameter than the anti-rotation section and furthermore the clamping member of the holding device must have a larger diameter than the force transmission element in order to engage this undercut 11. A similar undercut 11 is found in implants 200, 200'. The undercut 11 is necessary for the formation of the anti-rotation section. During that process, a narrow diameter bore is formed first in the dental implant and, subsequently, a larger diameter die, is pushed through the narrow diameter bore to stamp out the anti-rotation structure. In this way the die acts as a "cookie cutter" to remove sections of the implant radially adjacent to the narrow diameter bore in order to form the anti-rotation section. Prior to stamping, undercut 11 is formed underneath the site of the anti-rotation section so that material removed during the stamping process can fall into this undercut. Thus, the undercut 11 can contain debris from this procedure and, furthermore, may be partially and non-consistently deformed during the formation of the anti-rotation section by varying degrees in different implants. In contrast, according to the present disclosure, an undercut 240 distally positioned within the cavity 210 is separately and independently created via machining. This undercut 240 is not influenced by the die cutting procedure, as it is located distally remote from the anti-rotation section 222, and thus the dimensions of the undercut can be better controlled and more consistent, which ensures a satisfactory attachment to the holding device.

Figure 5B:
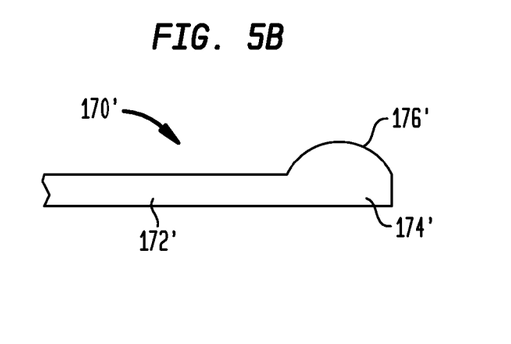
FIG. 5B is partial enlarged view of another embodiment of the resilient arm of the holding device shown in FIG. 5.

A person of ordinary skill in the art understands that the profile of the locking ends can be varied without departing from the spirit of the disclosure. For example, the locking end can have a convexly curved surface or a triangular surface. FIG. 5B illustrates another embodiment of a resilient arm 170', which includes a base 172' and a radially enlarged locking end 174' having a convexly curved surface 176'.

The above-described holding device provides an improved mechanism for holding and transferring dental implants, which can be stored in a preserving fluid, without affecting the property of the dental implant. Furthermore, the holding device is easier to operate and less costly to manufacture, as compared to the holding devices known in the prior art. It is noted that the holding device can be stored in a package with or without a storage fluid.

While the fundamental novel features of the disclosure have been shown and described, a person of ordinary skill in the art understands that various modifications, substitutions and changes in the form and details of the device can be made without departing from the spirit of the disclosure. It is therefore intended that the present invention not be limited to the exact forms and details described and illustrated herein, but falls within the scope of the appended claims.

What is claimed is:

1. A holding device for a dental implant, the holding device extending along a longitudinal axis and having a proximal end and a distal end, the holding device comprising:

an engagement section provided at the proximal end, adapted to engage a manipulating tool;
a retention section provided distally of the engagement section and adapted to engage a package; and
a securing section provided distally of the retention section and adapted to directly couple the holding device to the dental implant,
wherein:
the securing section comprises a force transmission element adapted to directly rotationally secure the dental implant and an attachment element provided distally of the force transmission element adapted to directly longitudinally secure the dental implant, the force transmission element being a substantially cylindrical body arranged coaxially with said longitudinal axis and having a non-circular cross section along its entire length, the force transmission element being solid over at least three quarters of its entire length and having a first projected area in a plane substantially perpendicular to the longitudinal axis, the attachment element having a second projected area in the plane, the second projected area being defined within the first projected area; such that no part of the attachment element extends beyond the radial circumference of the force transmission element; and
the attachment element comprises at least one resilient arm adapted to longitudinally secure the dental implant, the at least one resilient arm comprising a first operative configuration and a second compressed operative configuration.

2. The holding device according to claim 1, wherein the at least one resilient arm is integrally formed with the force transmission element.

3. The holding device according to claim 1, wherein the at least one resilient arm is positioned directly distal of the force transmission element.

4. The holding device according to claim 3 wherein the force transmission element comprises a distal end surface, the at least one resilient arm extending longitudinally from said distal end surface.

5. The holding device according to claim 1 wherein the force transmission element comprises a substantially cylindrical body and at least one longitudinally extending groove formed into the cylindrical body, the at least one groove being adapted to receive a longitudinally extending projection of the dental implant.

6. The holding device according to claim 5, wherein the force transmission element comprises a plurality of longitudinally extending grooves disposed circumferentially along the cylindrical body and evenly spaced about the longitudinal axis.

7. The holding device according to claim 1, wherein the at least one resilient arm comprises an elongated base longitudinally extending from the force transmission element, and a radially enlarged locking end at a distal end of the elongated base.

8. The holding device according to claim 7, wherein the radially enlarged locking end comprises a first sloped surface and a second oppositely sloped surface, both being angled with respect to the elongated base.

9. The holding device according to claim 7, wherein the radially enlarged locking end comprises a convexly curved surface.

10. The holding device according to claim 1, wherein the attachment element comprises a plurality of resilient arms disposed circumferentially along a predetermined circle and evenly spaced about the longitudinal axis.

11. The holding device according to claim 1, wherein the attachment element comprises a substantially cylindrical wall and the at least one resilient arm is formed from the cylindrical wall.

12. A combination of a holding device and a dental implant, the combination extending along a longitudinal axis and having a proximal end and a distal end,
the holding device comprising an engagement section provided at its proximal end and adapted to engage a manipulating tool, a retention section provided distally of the engagement section and adapted to engage a package, and a securing section provided distally of the retention section and adapted to couple the holding device to the dental implant, and
the dental implant comprising a cavity for at least partially receiving the securing section of the holding device;
wherein:
the securing section comprises a force transmission element adapted to directly rotationally secure the dental implant and an attachment element provided distally of the force transmission element adapted to directly longitudinally secure the dental implant,
the force transmission element being a substantially cylindrical body arranged coaxially with said longitudinal axis and having a non-circular cross section along its entire length, the force transmission element being solid over at least three quarters of its entire length and having a first projected area in a plane substantially perpendicular to the longitudinal axis, the attachment element having a second projected area in the plane, the second projected area being defined within the fist projected area such that no part of the attachment element extends beyond the radial circumference of the force transmission element;
the attachment element comprises at least one resilient arm adapted to longitudinally secure the dental implant, the at least one resilient arm comprising a first operative configuration and a second compressed operative configuration;
the cavity of the implant comprising an anti-rotation section adapted to engage with the force transmission element and, distal of and non adjacent to the anti-rotation section, an undercut, said undercut having a diameter less than that of the anti-rotation section.

13. The combination according to claim 12, wherein said at least one resilient arm is integrally formed with the force transmission element.

14. The combination according to claim 12, wherein the implant cavity further comprises, distal of the anti-rotation section, a cylindrical section having a smaller diameter than the anti-rotation section, wherein the undercut is formed within this cylindrical section.

15. The combination according to claim 14, wherein the cavity of the implant comprises a further undercut distally adjacent to the anti-rotation section and having a diameter equal to or greater than the anti-rotation section, the cylindrical section being directly distally adjacent to said further undercut.

16. The combination according to claim 12, wherein the at least the section of the force transmission element which is aligned with the anti-rotation section of the implant is solid.

17. The combination according to claim 12, wherein:
the force transmission element of the holding device comprises a substantially cylindrical body and at least one longitudinally extending groove formed into the cylindrical body; and
the dental implant comprises at least one longitudinally extending projection, which is operatively inserted into the at least one longitudinally extending groove to rotationally secure the force transmission element.

18. The combination according to claim 12, wherein:
the force transmission element of the holding device comprises a substantially cylindrical body and a plurality of longitudinally extending grooves formed into the cylindrical body, the plurality of longitudinally extending grooves being disposed circumferentially along the cylindrical body and evenly spaced about the longitudinal axis; and
the dental implant comprises a plurality of longitudinally extending projection, each of which is operatively inserted into a respective one of the plurality of longitudinally extending grooves to rotationally engage the force transmission element.

19. The combination according to claim 12, wherein:
the at least one resilient arm of the attachment element comprises an elongated base longitudinally extending from the force transmission element and a radially enlarged locking end at a distal end of the elongated base; which is operatively received in the undercut of the implant to longitudinally retain the dental implant.

20. The combination according to claim 19, wherein:
the radially enlarged locking end comprises a convexly curved surface; and
the dental implant comprises a cylindrical section, the cylindrical section adapted to operatively engage the convexly curved surface, such that the at least one resilient arm transforms between the first operative configuration and the second compressed operative configuration to permit the locking end to be operatively received within the undercut.

21. The combination according to claim 19, wherein the radially enlarged locking end comprises a first sloped surface and a second oppositely sloped surface, both being angled with respect to the elongated base.

22. The combination according to claim 12, wherein the attachment element comprises a plurality of resilient arms disposed circumferentially along a predetermined circle and evenly spaced about the longitudinal axis, each of the plurality of resilient arms comprising a first operative configuration and a second compressed operative configuration.

23. The combination according to claim 12, wherein the attachment element comprises a substantially cylindrical wall and the at least one resilient arm is formed from the cylindrical wall.

* * * * *